United States Patent [19]

Aikawa et al.

[11] Patent Number: 5,512,752
[45] Date of Patent: Apr. 30, 1996

[54] METHOD OF DETERMINING TYPE OF PLASTICS

[75] Inventors: Katsuaki Aikawa; Tadashi Shiratama, both of Saitama, Japan

[73] Assignee: Toa Electronics, Ltd., Tokyo, Japan

[21] Appl. No.: 181,517

[22] Filed: Jan. 13, 1994

[30] Foreign Application Priority Data

Jan. 14, 1993 [JP] Japan .................................. 5-021865

[51] Int. Cl.$^6$ ................................................ G01N 21/35
[52] U.S. Cl. ............................. 250/339.12; 250/339.11; 250/341.8
[58] Field of Search .................. 250/339.11, 339.12, 250/341.8

[56] References Cited

U.S. PATENT DOCUMENTS

| | | | |
|---|---|---|---|
| 5,015,856 | 5/1991 | Gold | 250/339.09 |
| 5,041,996 | 8/1991 | Emering | 364/550 |
| 5,134,291 | 7/1992 | Ruhl, Jr. et al. | 250/339.11 |
| 5,150,307 | 9/1992 | McCourt et al. | 364/478 |
| 5,206,510 | 4/1993 | Wolf et al. | 250/339.08 |

FOREIGN PATENT DOCUMENTS

WO9207332  4/1992  WIPO.

OTHER PUBLICATIONS

Weyer, L. G., "Utilizing Zero Crossover Points in the Near Infrared Reflectance Analysis of Industrial Polymers," *Journal of Applied Polymer Science*, 31:5 (1986), pp. 2417–2431.

European Search Report concerning European Patent Application No. EP 94300251.9 dated May 4, 1994 (2 pages).

*Primary Examiner*—Constantine Hannaher
*Attorney, Agent, or Firm*—Panitch Schwarze Jacobs & Nadel

[57] ABSTRACT

A method is provided for determining the type of an unknown plastic including the steps of irradiating an unknown plastic with near-infrared rays within a prescribed measurement wavelength range to measure an absorption spectrum, calculating the differential spectrum of the unknown plastic, measuring the differential spectrum at prescribed measurement intervals, determining the class of the differential spectrum by determining whether each measurement is on a plus-side, a minus-side or any other side, comparing the class of the differential spectrum measurement at each interval with a class of a differential spectrum measurement previously determined for each of the intervals over the range for a plurality of plastics of known types, and determining the type of the unknown plastic as the plastic having the highest class agreement ratio.

13 Claims, 8 Drawing Sheets

METHOD OF DETERMINING TYPE OF PLASTICS

BACKGROUND OF THE INVENTION

1. Field of the Invention

The present invention relates to a method of determining the type of plastics. More particularly, the present invention relates to a method of determining the type of plastics, which, in disposing of or recycling diverse waste of plastics such as plastic bottles for soft drink and plastic packages of foods, is adapted to be used for classifying plastic waste by materials.

2. Prior Art

Various types of plastics including plastic bottles for soft drink and plastic packages of foods are rejected as waste after use in large quantities and are disposed of by incineration or dumping for reclamation.

A problem is however that incineration is not suitable for some types of plastics because the incinerator is damaged, and it is becoming more and more difficult to find new incinerating yards and land for reclamation. It is therefore tried now to manufacture petroleum and other fuel from plastic waste, or to recycle waste by bringing back to the original plastic materials for each type of plastics.

Under such circumstances, it is becoming more important than ever to determine the type of plastics and classify plastic waste into individual types.

The conventional methods already in industrial use for classifying plastics include a method using the difference in specific gravity between different types of plastics and a method of identifying polyvinyl chloride based on X ray.

In the method based on specific gravity, however, separation is difficult between polyethylene and polypropylene and between polyvinyl chloride and polyethylene terephthalate, because of the relatively slight difference in specific gravity, and another problem is that specific gravity of plastics varies as a result of surface wetting of plastics or kneading with pigment or filler, so that these methods are far from being satisfactory.

In the method based on X ray also, use of radiation poses problems in safety and management, and in addition, polyvinyl chloride is the only plastics that this method can identify and classify, so that this cannot be practicable.

SUMMARY OF THE INVENTION

An object of the present invention is therefore to provide a method determining the type of plastics, which is suitably applicable for simply and rapidly determining the type of plastics to classify plastics waste into different materials.

The above-mentioned object is achieved by the method of determination of the present invention. In summary, the present invention provides a method of determining the type of plastics, which comprises the steps of irradiating near-infrared rays to an unknown plastics to measure absorption spectrum, calculating the differential spectrum thereof, measuring said differential spectrum at prescribed intervals of wavelength over a region of measurement wavelengths, determining whether a differential spectrum at each of the measurement wavelengths is on the plus-side, minus-side or any other side, and comparing the class of the differential spectrum for each measurement wavelength with that of the differential spectrum previously determined for a plastics which type is known, thereby determining the type of said unknown plastics.

According to the present invention, the method of determining the type of plastics comprises determining the maximum absolute value of differential spectrum in the above-mentioned measurement wavelength region, providing a determination reference region marked off by setting a certain value selected with this maximum value in both plus and minus directions to standardize the differential spectrum, whereby it is possible to determine whether the differential spectrum is on the plus-side, on the minus-side, or on any other side depending upon whether it is over, under or within the above-mentioned reference region for determination. The differential spectrum may be of any degree, but should preferably be a first-order or secondary differential spectrum.

DETAILED DESCRIPTION OF THE PREFERRED EMBODIMENTS

Figure 1:
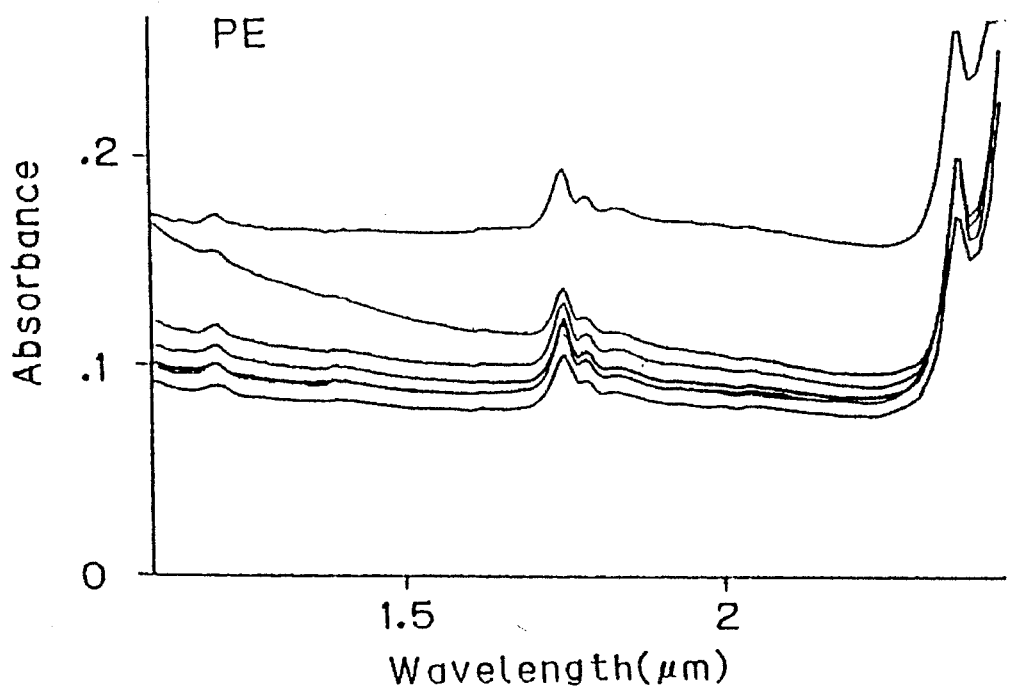
FIG. 1 is a graph illustrating NIR (near infrared) spectra of polyethylene used for the preparation of a reference file in an embodiment of the method of determination of the present invention.
Figure 2:
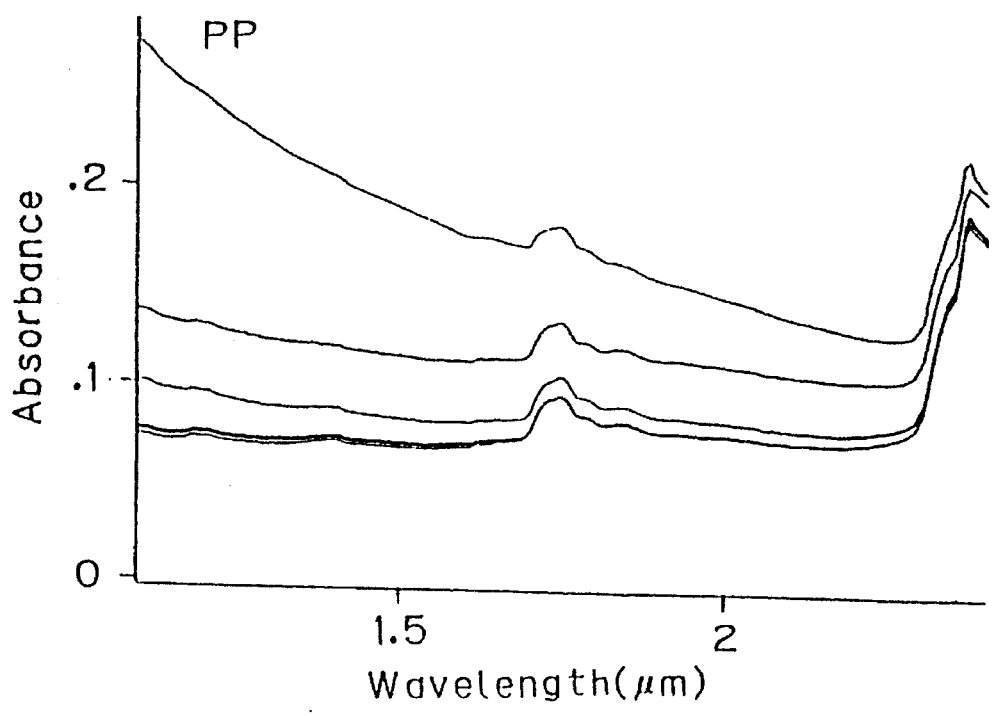
FIG. 2 is a graph illustrating NIR spectra of polypropylene used for the same purpose as in FIG. 1.
Figure 3:
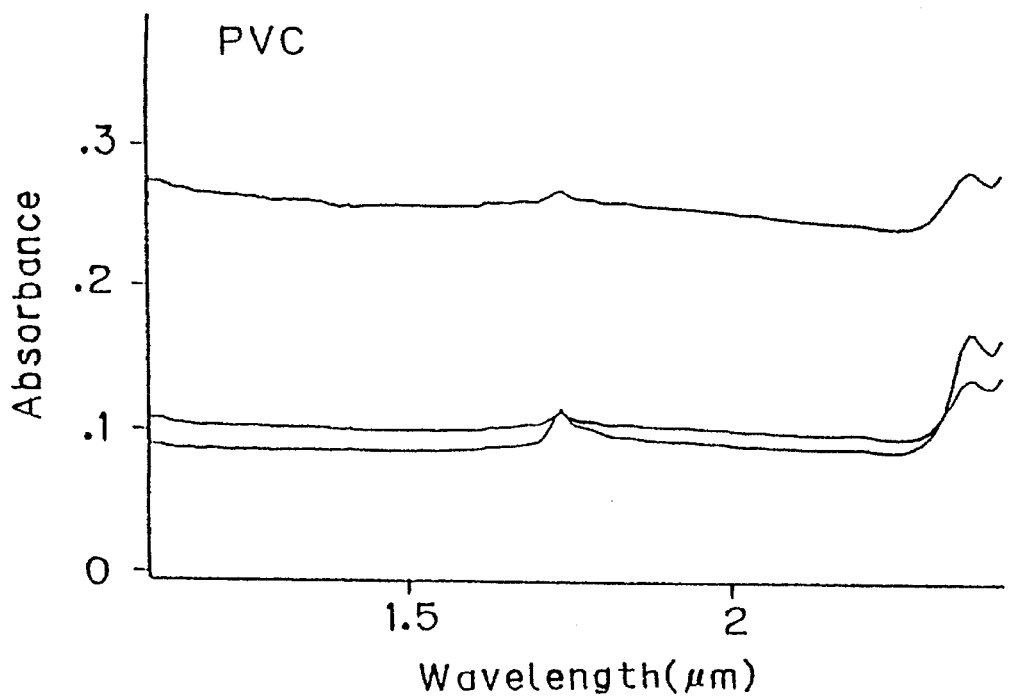
FIG. 3 is a graph illustrating NIR spectra of polyvinyl chloride used for the same purpose as in FIG. 1.
Figure 4:
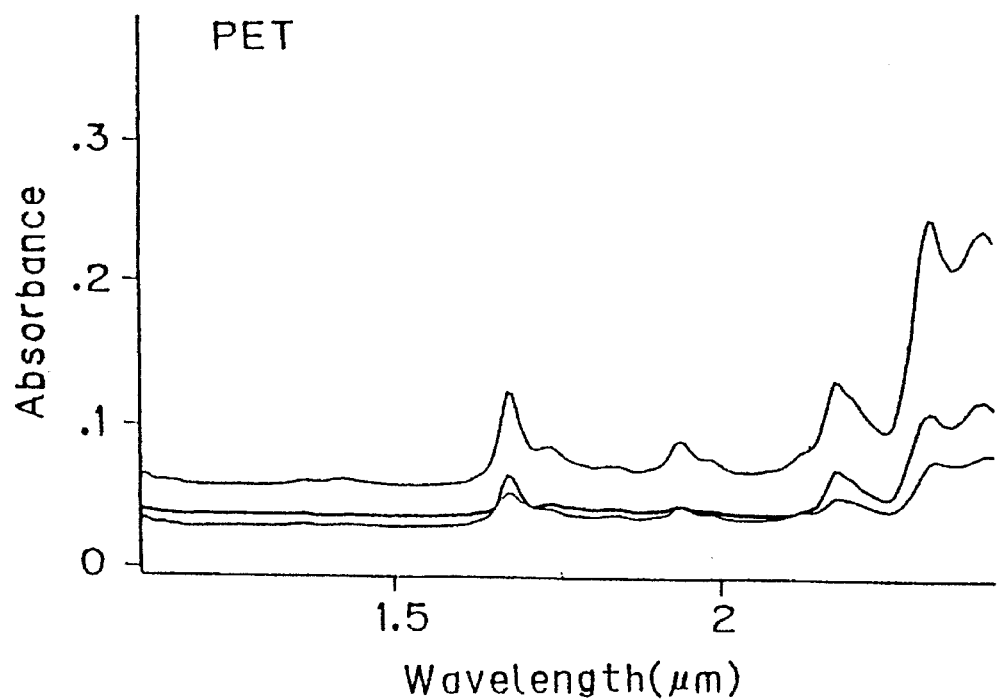
FIG. 4 is a graph illustrating NIR spectra of polyethylene terephthalate used for the same purpose as in FIG. 1.
Figure 5:
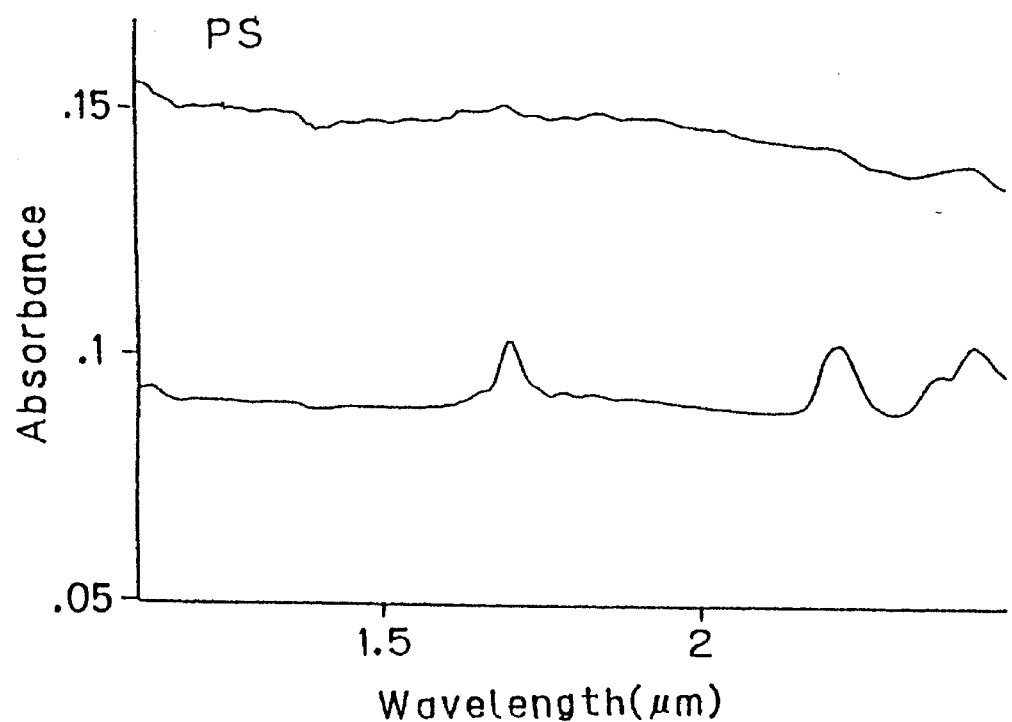
FIG. 5 is a graph illustrating NIR spectra of polystyrene used for the same purpose as in FIG. 1.
Figure 6:
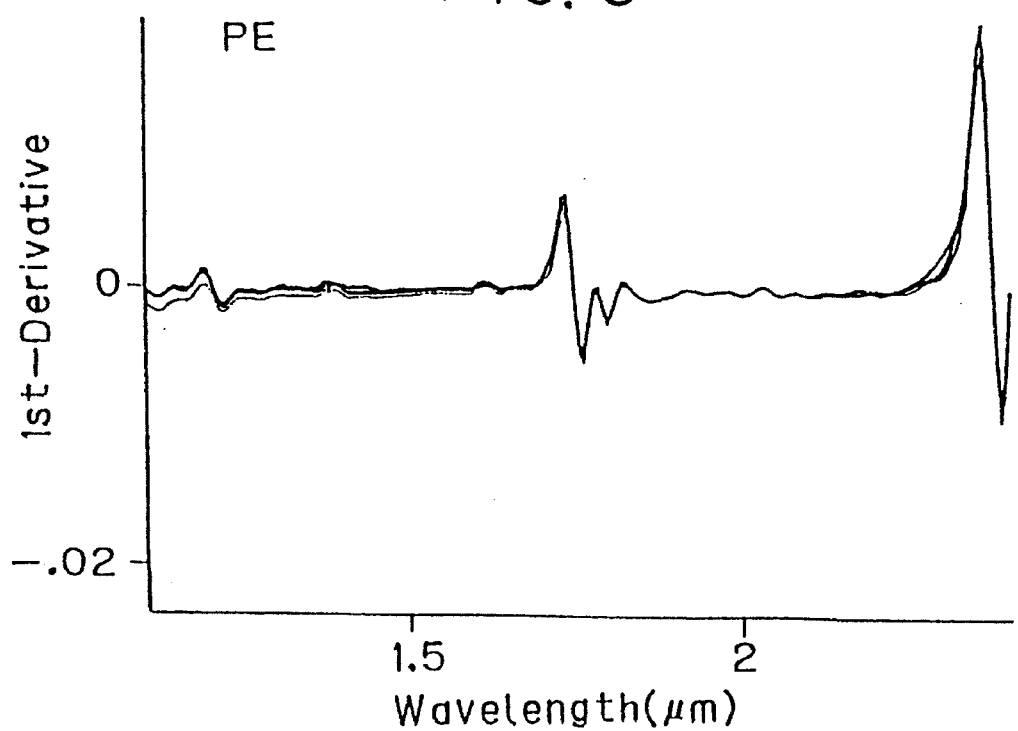
FIG. 6 is a graph illustrating first-derivative NIR spectra of polyethylene shown in FIG. 1.
Figure 7:
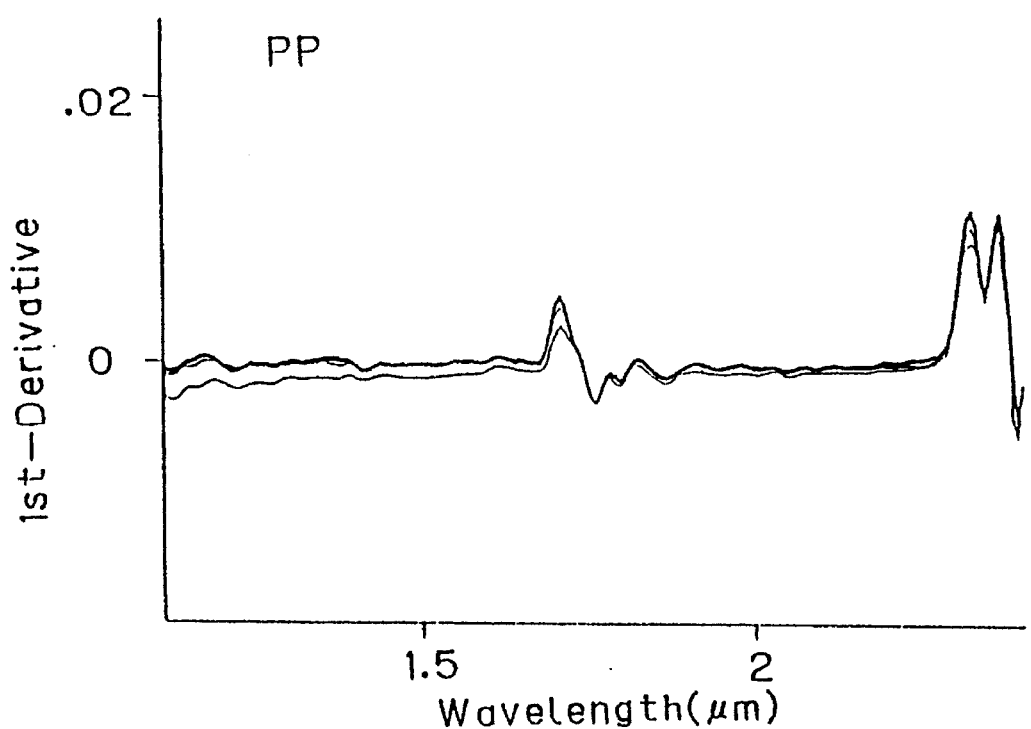
FIG. 7 is a graph illustrating first-derivative NIR spectra of polypropylene shown in FIG. 2.
Figure 8:
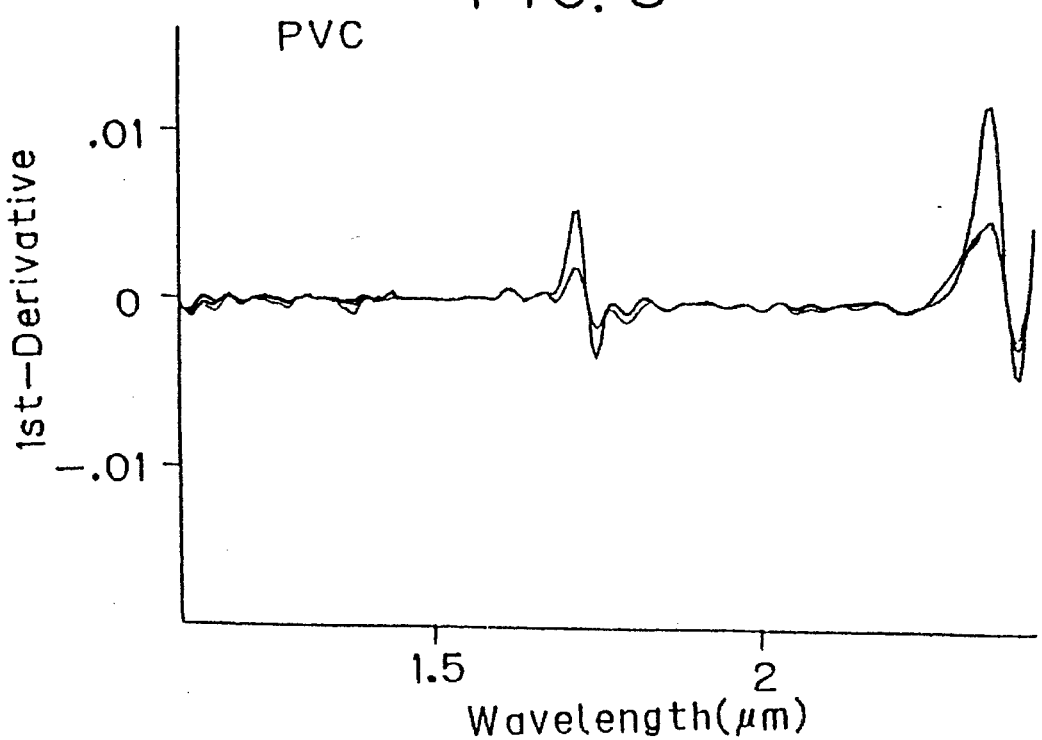
FIG. 8 is a graph illustrating first-derivative NIR spectra of polyvinyl chloride shown in FIG. 3.
Figure 9:
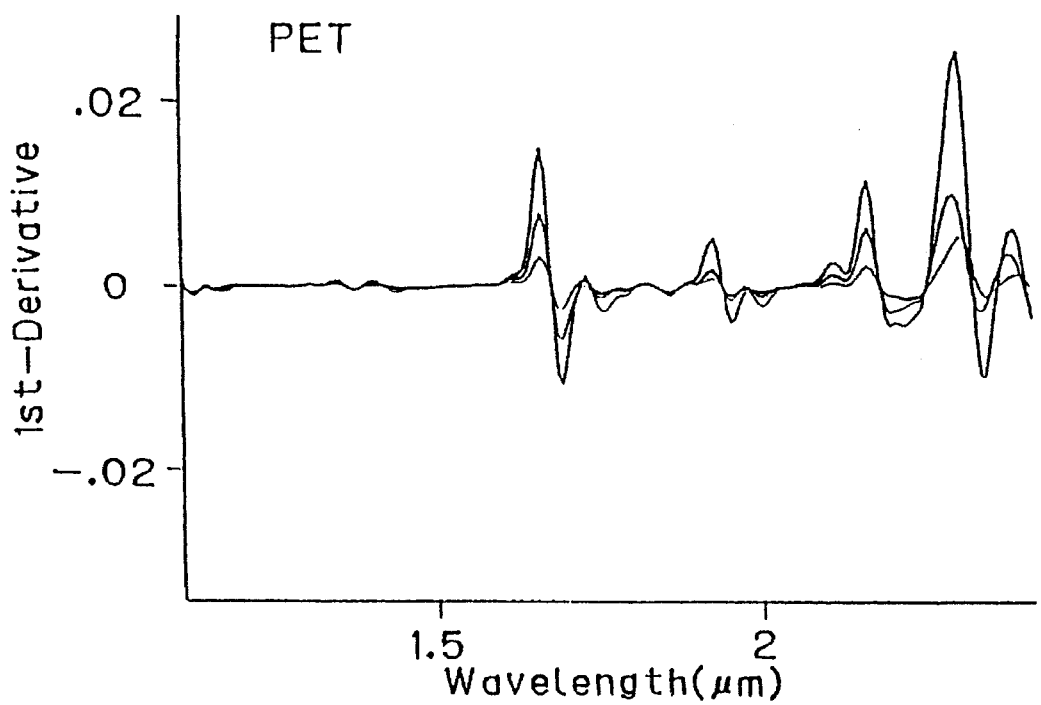
FIG. 9 is a graph illustrating first-derivative NIR spectra of polyethylene terephthalate shown in FIG. 4.
Figure 10:
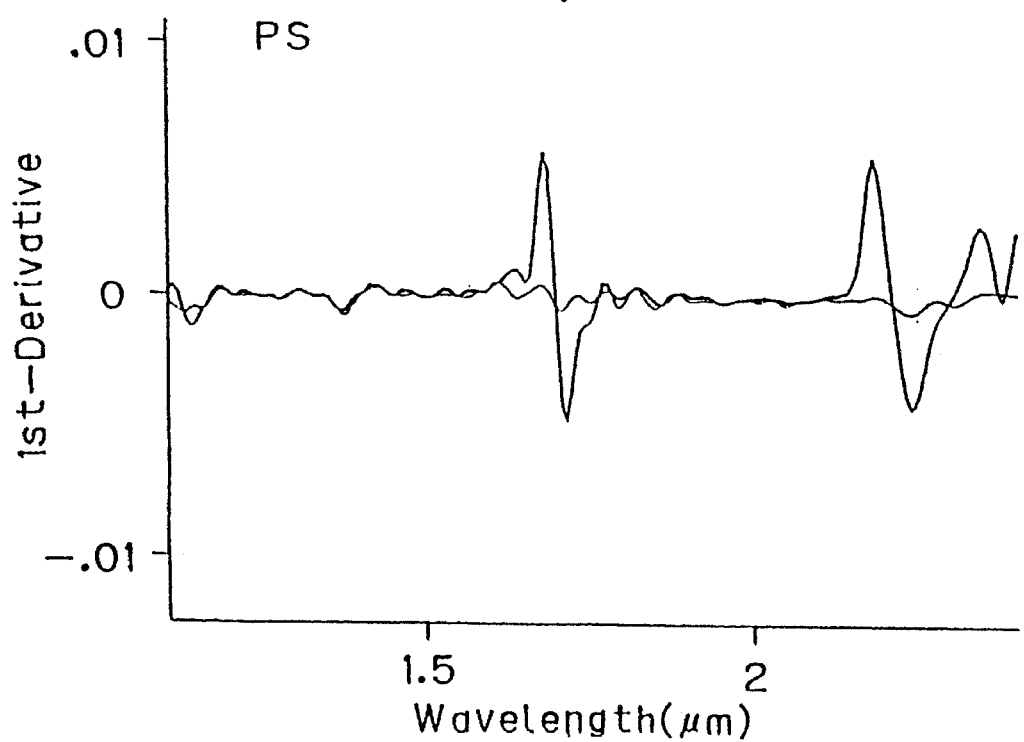
FIG. 10 is a graph illustrating first-derivative NIR spectra of polystyrene shown in FIG. 5.
Figure 11:
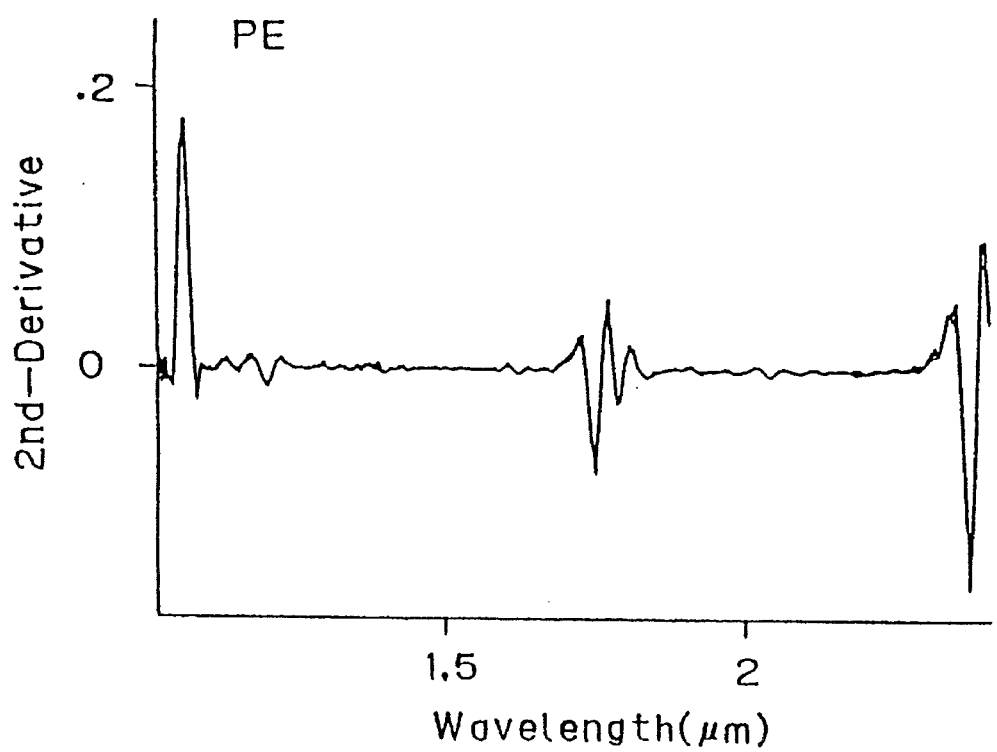
FIG. 11 is a graph illustrating second-derivative NIR spectra of polyethylene shown in FIG. 1.
Figure 12:
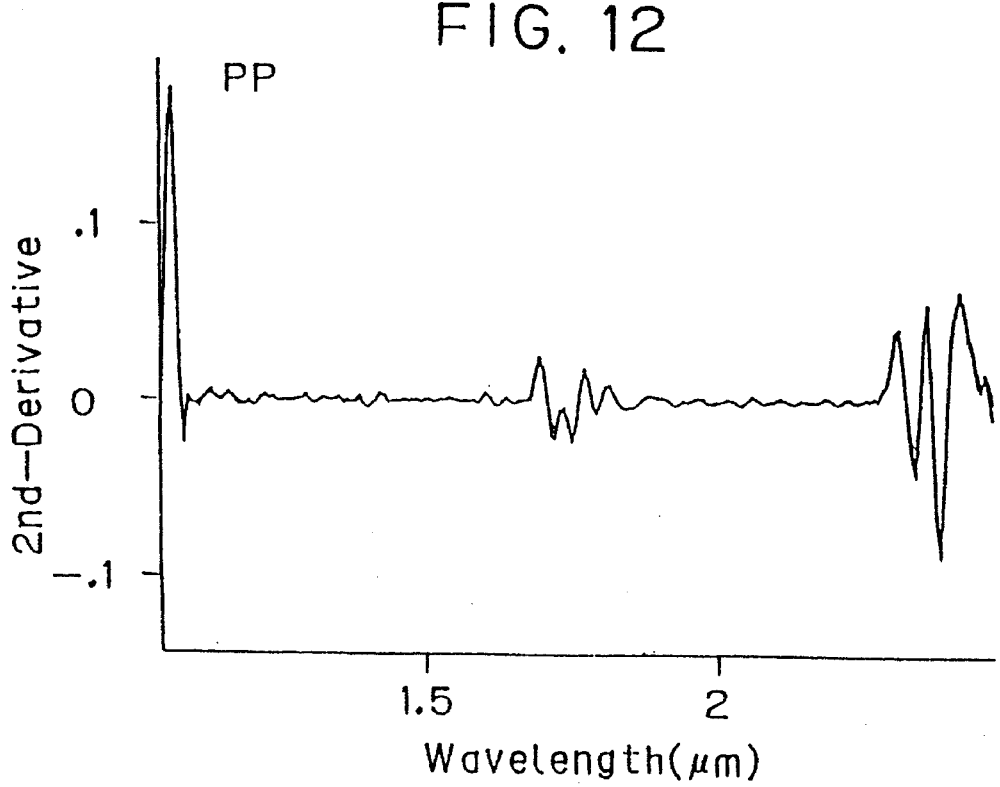
FIG. 12 is a graph illustrating second-derivative NIR spectra of polypropylene shown in FIG. 2.
Figure 13:
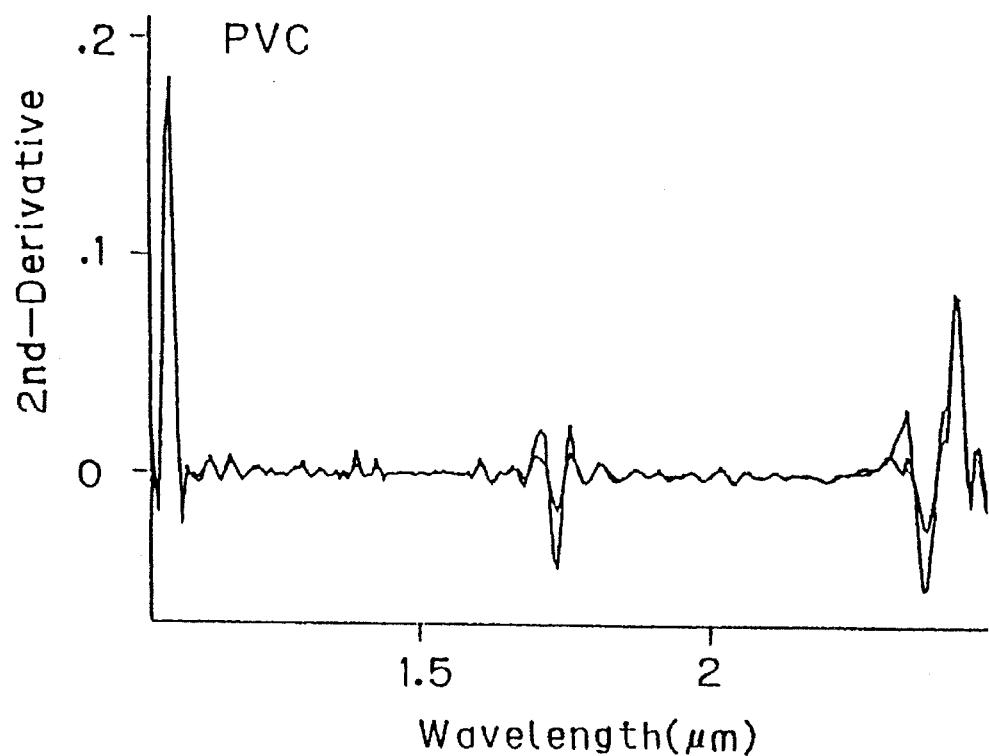
FIG. 13 is a graph illustrating second-derivative NIR spectra of polyvinyl chloride shown in FIG. 3.
Figure 14:
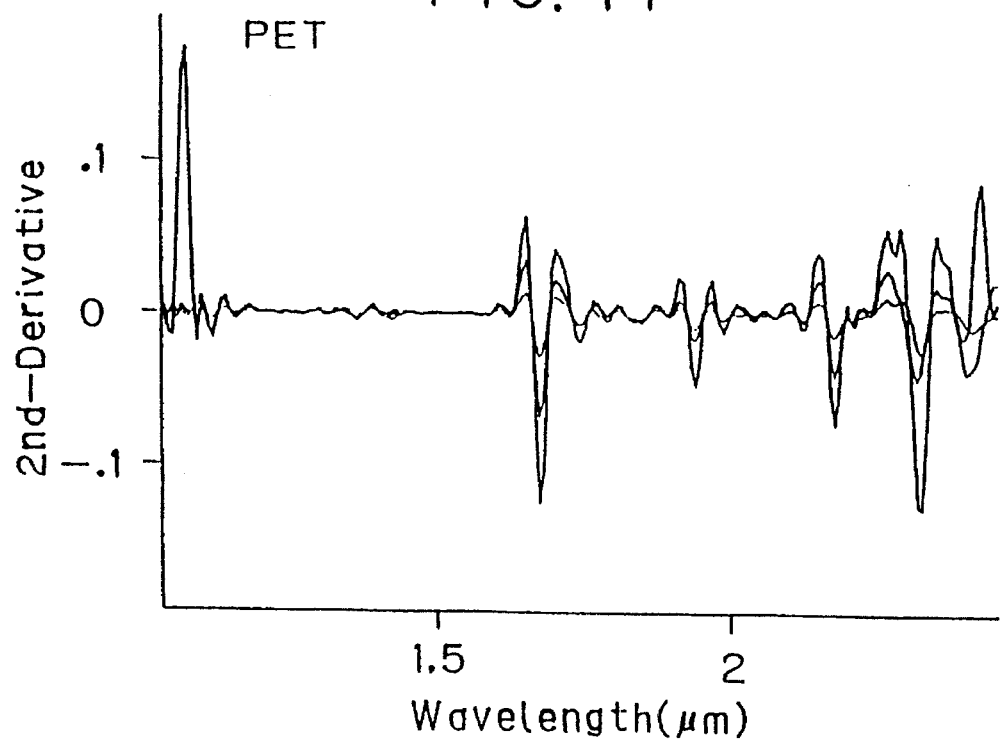
FIG. 14 is a graph illustrating second-derivative NIR spectra of polyethylene terephthalate shown in FIG. 4.
Figure 15:
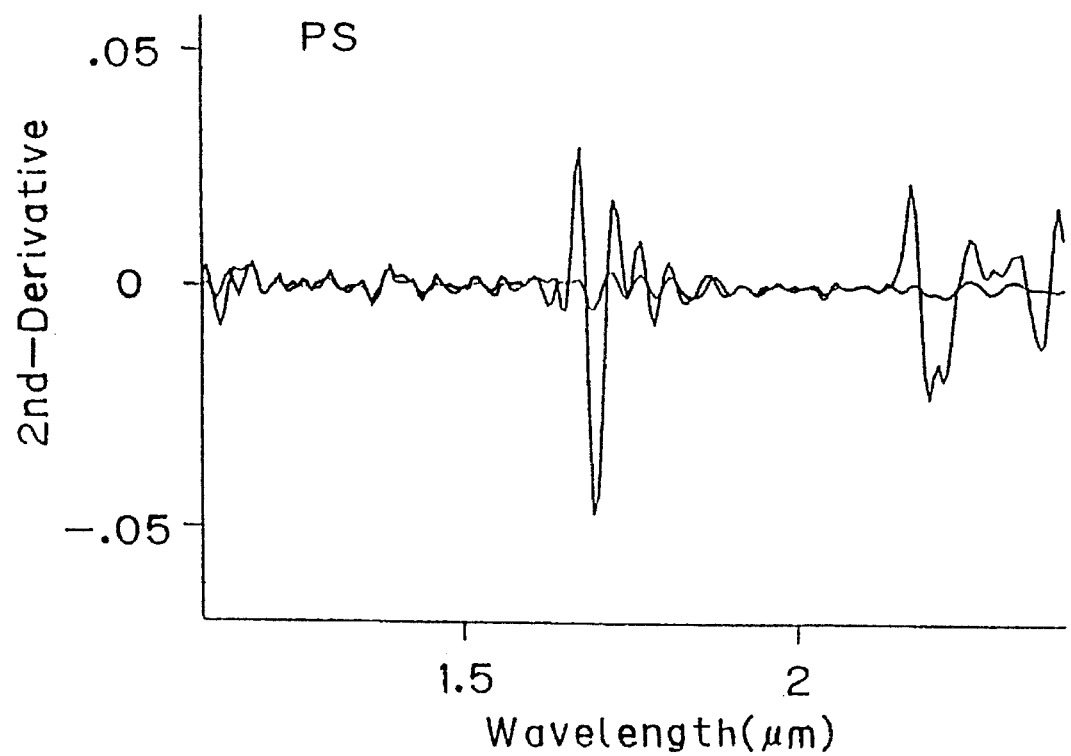
FIG. 15 is a graph illustrating second-derivative NIR spectra of polystyrene shown in FIG. 5.

FIGS. 1 to 5 are graphs illustrating NIR spectra of plastics used for the preparation of reference files in an embodiment of the method of determination of the present invention. The NIR spectra were measured from a transmitted beam of near-infrared rays irradiated. FIG. 1 shows NIR spectra obtained by irradiating near-infrared rays while continuously scanning within a wavelength region of from 1 to 2.5 μm for seven kinds of polyethylene (PE). Similarly, FIG. 2 shows NIR spectra determined for five kinds of polypropylene (PP); FIG. 3, three kinds of polyvinyl chloride (PVC); FIG. 4, three kinds of polyethylene terephthalate (PET); and FIG. 5, two kinds of polystyrene (PS).

There are present, in the near-infrared region, overtones and combination tones of absorbance of the infrared region, which are providing much information for qualitative and quantitative analyses of moisture and organic substances. Abundance of information however forms noise signals in the analysis of a target constituent and this often hinders smooth analysis. In spectroscopic analysis in near-infrared region, therefore, a statistical technique such as multivariate analysis is employed to derive information which meets the purpose from the available NIR spectra. That is, analysis of NIR spectra is now an important element in the spectroscopic analysis in the near-infrared region.

In the present invention, therefore, a method of determining the type of plastics through a simple spectral analysis was achieved while avoiding to adopt such a complicated statistical technique. More specifically, the method comprises measuring NIR spectrum of the target plastics, calculating a differential spectrum, and determining the type of plastics from whether the wavelength region containing the peak of the resultant differential spectrum (differential peak) agrees or not.

The technique of determining a differential spectrum such as a first-derivative or a second-derivative through measurement of NIR spectrum is a known one, and permits expectation of such effects as: (1) eliminating biases present over the entire region of measurement, such as the influence of opacity or stain of the sample of measurement; (2) converting superposed spectra into signals easier to analyze; and (3) there being present a zero-crossover point on the wavelength axis.

First-derivatives derived from the NIR spectra shown in FIGS. 1 to 5 are illustrated in FIGS. 6 to 10, and second-derivatives thereof, in FIGS. 11 to 15. In the first-derivatives and the second-derivatives, biases present throughout the entire measurement wavelength region as observed in the NIR spectra have been eliminated, and superposed peaks have been converted into a waveform easier to analyze. A zero-crossover point is existent on the wavelength axis.

This zero-crossover point is a point where the waveform curve of the NIR spectrum intersects the wavelength axis having a differential value of zero. In the first-derivative, this corresponds to the maximum peak wavelength of NIR spectrum, and in the second-derivative, to the wavelength at which a point of inflection of NIR spectrum appears. The zero-crossover point in a differential spectrum is therefore a singular point of function intrinsic to a particular type of plastics, irrespective of the thickness of density of the particular plastics.

It is estimated from this fact that when this zero-crossover point differs in position between two plastics, i.e., if the wavelength regions are different of the peak of differential spectrum (differential peak) appearing between the zero-crossover points, the two plastics are of different types, and if identical on the other hand, these must be plastics of the same type.

As is clear from FIGS. 6 to 10 and 11 to 15, the wave-length region in which the differential peak appears differs with the type of plastics for both first-derivatives and second-derivatives. It is therefore possible to determine the type of an unknown plastics by previously determining the wavelength region in which the differential peak appears for a plastics of a known type, and seeing whether or not the wavelength region in which the differential peak appears of an unknown plastics agrees with it.

The method of a first embodiment of the present invention comprises the following steps. In the description hereafter, data processing is accomplished by a computer connected to a near-infrared spectrometer.

(1) First, measuring continuously the near-infrared absorption spectrum in a prescribed wavelength region such as from 1 to 2.5 µm for a plastics of a known type, determining first-derivative or second-derivative thereof, and determining the differential spectrum at prescribed intervals of wavelength within a range of from several nm to 10 nm, at intervals of 6 nm for example, over the entire measurement wavelength region, thereby determining the class as to whether the differential spectrum for each of the measurement wavelengths is on the plus-side, minus-side or any other side. This is applied to some plastics of the same category, such as seven kinds of polyethylene, and classes of the individual differential spectra are labelled with signs "+1," "–1" or "0," depending upon whether that class of differential spectra is on the plus-side, minus-side or on any other side. Similarly, the same steps are followed also for other types of plastics.

(2) Then, preparing a classification table showing classification data of differential spectra with corresponding numbers of measurement wavelengths as shown in Table 1, and storing the prepared table in the memory as a reference file for each type of plastics. Table 1 shows 256 data obtained by measuring a measurement wavelength region of 1 to 2.5 µm at intervals of wavelength width of 6 nm.

TABLE 1

| Data No. | 0 | 1 | 2 | 3 | ... | n − 1 | n | n + 1 | ... | 253 | 254 | 255 |
|---|---|---|---|---|---|---|---|---|---|---|---|---|
| Label | 0 | 0 | +1 | +1 | | −1 | −1 | 0 | | 0 | 0 | 0 |

(3) Conducting the same operation also for plastics of an unknown type, continuously measuring NIR spectrum to determine the differential spectrum, determining the differential spectrum at equal intervals of wavelength over the range of measurement wavelengths, determining the class as to whether the differential spectrum of each measurement wavelength is on plus-side, minus-side, or on any other side to label "+1," "–1" and "0," and preparing a classification table showing classification data of differential spectra with corresponding data numbers. It is assumed that a classification table as shown in Table 2 is obtained.

TABLE 2

| Data No. | 0 | 1 | 2 | 3 | ... | n − 1 | n | n + 1 | ... | 253 | 254 | 255 |
|---|---|---|---|---|---|---|---|---|---|---|---|---|
| Label | 0 | 0 | +1 | +1 | | 0 | −1 | −1 | | 0 | 0 | 0 |

(4) Then, comparing all the data of the classification table of an unknown plastics with all the data of the classification table of reference file for each data No. one by one to determine the number of data showing agreement of labels. Conducting this operation for all the reference files of the previously stored known plastics.

(5) Then, determining the ratio of the number of data showing labels in agreement to all the number of data, investigating the highest agreement ratio, and determining that the plastics of the reference file of the highest agreement ratio is the type of the unknown plastics.

The use of the above-mentioned agreement ratio means determination of the degree of agreement of the wavelength region in which the differential peak of the unknown plastics appears with the wavelength region in which the differential peak of the known plastics appears. The plastics showing the highest agreement ratio is the type of the unknown plastics, thus the type of the unknown plastics is determined.

According to the above-mentioned embodiment of the method of the present invention, therefore, it is possible to simply and rapidly determine the type of an unknown plastics.

Figure 16:
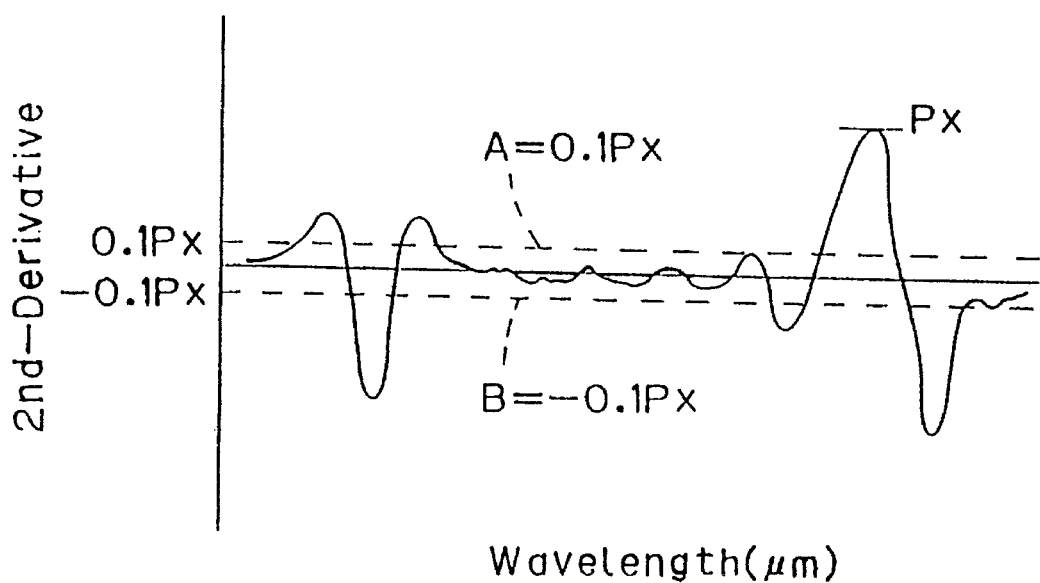
FIG. 16 is a descriptive view illustrating setting of standard region of determination of class at individual measurement wavelengths on differential spectra in the method of the second embodiment of the present invention.

The second embodiment of the present invention, which permits further improvement of the determination accuracy and is therefore more preferable, comprises the following steps;

(1) First, for the purpose of increasing the determining accuracy of the class of first-derivative or second-derivative for each measurement wavelength, determining the maximum value (assumed to be Px) of the absolute value of differential spectrum in the measurement wavelength region, as shown in FIG. 16, and setting a determination standard region marked off by certain plus and minus values selected with the maximum value to standardize the differential spectrum, for example, taking 10% of the maximum value: A=0.1 Px and B=−0.1 Px (a region surrounded by lines parallel to the wavelength axis passing through differential values A and B in FIG. 16).

(2) Then, labelling the class of the differential spectrum for each measurement wavelength as "+1," "−1" or "0," respectively, depending upon whether the differential spectrum is over, under or within the determination standard region, preparing a classification table containing class data of the differential spectrum with corresponding data number, and storing the table as the reference file for each class of plastics.

(3) Conducting the same operation for the plastics of an unknown type, labelling the class of the differential spectrum for each measurement wavelength as "+1," "−1" or "0," respectively, depending upon whether the differential spectrum is over, under or within the determination standard region, and preparing a classification table containing class data of the differential spectrum with corresponding data numbers.

(4) Then, comparing data of the classification table of the unknown plastics with data of the classification table of reference file for each data No. one by one to determine the number of data showing lables in agreement. Such comparison is not made, however, for data numbers labelled "0" in the reference file. Conducting this operation for all the reference files of the previously stored known plastics.

(5) Then, determining the ratio of the number of data showing labels in agreement to the total number of data (naturally excluding the number of data labelled "0"), investigating the highest agreement ratio, and determining that the plastics of the reference file of the highest agreement ratio is the type of the unknown plastics.

According to this second embodiment, the class of differential spectrum for each measurement wavelength is determined by setting the determination standard region marked off with certain plus and minus values with the maximum absolute value of differential spectrum to standardize the differential spectrum, while avoiding comparison of data labelled "0" which have a small S/N ratio of waveform (differential signal) because of the slight value of differential spectrum (differential value), thus permitting remarkable improvement of the determining accuracy of the class of plastics.

Both the above-mentioned embodiment have comprised continuously measuring NIR spectrum within a prescribed wavelength region to determine the differential spectrum thereof, and measuring the differential spectrum at prescribed intervals of wavelength over a region of measurement wavelengths, thereby determining the class of the differential spectra at each measurement wavelength. The present invention is not however limited to these embodiments, but the kind of differential spectrum at each measurement wavelength may be determined, by measuring NIR spectrum at prescribed intervals of wavelength from the very beginning over a prescribed region of wavelengths, from differential spectra thereof. In the above-mentioned embodiments, a classification table of differential spectra at each measurement wavelength has been prepared for an unknown plastics, and data of this classification table have been compared with data of a classification table of reference file. It is not always necessary, however, to compare the class data of differential spectra of the unknown plastics after preparing the classification table, but comparison with the data of the classification table of reference file may be made every time a class data of the differential spectrum at each measurement wavelength is obtained. A first-derivative or second-derivative has been used in the above-mentioned embodiments, but a similar operation may be accomplished through determination of a tertiary or a higher-degree differential spectrum. The absorption spectrum can be measured from a transmitted beam or reflected beam of near-infrared rays irradiated to the target plastics.

EXAMPLE

Now, the present invention will be described further in detail by means of an example.

In accordance with the present invention, NIR spectrum was continuously measured in a wavelength region of from 1 to 2.5 μm for plastics samples including PE (polyethylene), PET (polyethylene terephthalate), PP (polypropylene), PVC (polyvinyl chloride) and PS (polystyrene) in the form of plastics bags and the like. Second-derivative was determined from the results of measurement, and the differential spectrum was measured at intervals of wavelength of 6 nm. With the use of the method of the second embodiment, the class of the differential spectrum for each measurement wavelength was determined. The labels of these class data were compared with the lables of all the data numbers in the classification table of reference file previously prepared for secondary differential spectra shown in FIGS. 11 to 15, except for the data numbers labelled "0," to determined the type of plastics samples from the agreement ratios. The types, agreement ratios and the results of determination for these plastics samples are shown in Table 3.

TABLE 3

| Plastic samples | Type | Thickness (mm) | Color, etc. | Agreement ratio (%) | | | | | Determination based on agreement ratio |
|---|---|---|---|---|---|---|---|---|---|
| | | | | PE | PP | PVC | PET | PS | |
| Plastics bag | PE | 0.05 | White | 84 | 50 | 44 | 11 | 33 | PE |
| Plastics bottle | PET | 0.4 | Transparent blue | 28 | 33 | 32 | 92 | 24 | PET |
| Packaging film | PVC | 0.05 | | 52 | 46 | 88 | 29 | 42 | PVC |
| Reagent bottle | PP | 1 | White | 56 | 100 | 56 | 18 | 21 | PP |
| Toilet water container | PS | 1.8 | Transparent white | 29 | 25 | 36 | 38 | 82 | PS |

As shown in Table 3, each of the plastics samples shows a maximum agreement ratio of at least 70% at a point corresponding to the type of plastics employed, thus demonstrating that the type of plastics was accurately determined from the agreement ratio.

As described above, the method of the present invention comprises the steps of irradiating near-infrared ray to a plastics of an unknown type to measure NIR spectrum, determining the differential spectrum thereof, measuring the differential spectrum at a prescribed wavelength width in a measurement wavelength region, determining the class of whether the differential spectrum at each measurement wavelength is on the plus-side, minus-side or any other side, and comparing the determined class with the class of the previously determined differential spectra of plastics of known types, thereby determining the type of the unknown plastics, thus permitting simple and rapid determination. The method of the present invention is suitably applicable for the determination of the type of plastics in various areas, including classification of plastics waste into individual materials.

What is claimed is:

1. A method of determining a type of an unknown plastic, comprising the steps of:
   (a) irradiating the unknown plastic with near-infrared rays to measure an absorption spectrum of the unknown plastic over a measurement wavelength range within a near infrared-region;
   (b) calculating and measuring a differential spectrum of the unknown plastic at equal intervals of wavelength of up to 10 nm to provide a differential spectrum measurement for each measurement interval;
   (c) determining a class of the differential spectrum measurement for each interval as to whether each differential spectrum measurement is positive, negative or zero;
   (d) comparing the class of the differential spectrum measurement of the unknown plastic with a class of a differential spectrum measurement previously determined for each of a plurality of plastics of known types for each interval;
   (e) calculating a ratio of agreement for each known plastic by dividing the number of times the class of the differential spectrum measurement of the unknown plastic agrees with the class of the differential spectrum measurement of each known plastic by the total number of intervals compared; and
   (f) determining the type of the unknown plastic as the known plastic having the highest ratio of agreement.

2. The method of determining the type of an unknown plastic as claimed in claim 1, wherein said spectrum is measured for a transmitted beam of the near-infrared rays irradiated onto said unknown plastic.

3. The method of determining the type of an unknown plastic as claimed in claim 2, wherein said plastics of known types include polyethylene, polypropylene, polyvinyl chloride, polyethylene terephthalate, and polystyrene.

4. The method of determining the type of an unknown plastic as claimed in claim 1, wherein said spectrum is measured for a reflected beam of the near-infrared rays irradiated on said unknown plastic.

5. The method of determining the type of an unknown plastic as claimed in claim 4, wherein said plastics of known types include polyethylene, polypropylene, polyvinyl chloride, polyethylene terephthalate, and polystyrene.

6. The method of determining the type of an unknown plastic as claimed in claim 1, wherein said differential spectrum is a first-derivative or a second-derivative.

7. The method of determining the type of an unknown plastic as claimed in claim 6, wherein said plastics of known types include polyethylene, polypropylene, polyvinyl chloride, polyethylene terephthalate, and polystyrene.

8. The method of determining the type of an unknown plastic as claimed in claim 1, wherein said plastics of known types include polyethylene, polypropylene, polyvinyl chloride, polyethylene terephthalate, and polystyrene.

9. A method of determining a type of an unknown plastic comprising the steps of:
   (a) irradiating the unknown plastic with near-infrared rays to measure an absorption spectrum of the unknown plastic over a measurement wavelength range within a near-infrared region;
   (b) calculating and measuring a differential spectrum of the unknown plastic at equal intervals of wavelength of up to 10 nm to provide a differential spectrum measurement for each measurement interval;

(c) determining a maximum absolute value of the differential spectrum measurements within the measurement wavelength range to provide a standard determination region marked off in a positive and a negative direction by a certain value selected with the maximum absolute value;

(d) determining a class of the differential spectrum measurement for each interval as to whether each differential spectrum measurement is over, under, or within the standard determination region;

(e) comparing the class of the differential spectrum measurement of the unknown plastic with a class of a differential measurement previously determined for each of a plurality of plastics of known types for each interval, wherein only the classes of the differential spectrum measurements of the known plastics which are over and under the standard region are to be compared;

(f) calculating a ratio with which the class of the differential spectrum measurement of the unknown plastic agrees with the class of the differential spectrum measurement of each known plastic; and (g) determining the type of the unknown plastic from among the known plastics as the plastic having the highest ratio of agreement.

10. The method of determining the type of an unknown plastic as claimed in claim 9, wherein said spectrum is measured for a transmitted beam of the near-infrared rays irradiated onto said unknown plastic.

11. The method of determining the type of an unknown plastic as claimed in claim 9, wherein said spectrum is measured for a reflected beam of the near-infrared rays irradiated onto said unknown plastic.

12. The method of determining the type of an unknown plastic as claimed in claim 9, wherein said differential spectrum is a first-derivative or a second-derivative.

13. The method of determining the type of an unknown plastic as claimed in claim 9, wherein said plastics of known types include polyethylene, polypropylene, polyvinyl chloride, polyethylene terephthalate, and polystyrene.

* * * * *